(12) United States Patent
Mitchell et al.

(10) Patent No.: US 9,370,384 B2
(45) Date of Patent: Jun. 21, 2016

(54) BONE FIXATION ROD AND IMPLANTATION DEVICE FOR INSERTION THEREOF

(71) Applicant: Beacon Biomedical, LLC, Jupiter, FL (US)

(72) Inventors: Dale Mitchell, Jupiter, FL (US); Daxes Banit, Warner Robins, GA (US)

(73) Assignee: Beacon Biomedical, LLC, Jupiter, FL (US)

( * ) Notice: Subject to any disclaimer, the term of this patent is extended or adjusted under 35 U.S.C. 154(b) by 0 days.

(21) Appl. No.: 14/153,768

(22) Filed: Jan. 13, 2014

(65) Prior Publication Data

US 2014/0128931 A1 May 8, 2014

Related U.S. Application Data

(63) Continuation of application No. 13/107,189, filed on May 13, 2011, now Pat. No. 8,628,535.

(60) Provisional application No. 61/334,643, filed on May 14, 2010.

(51) Int. Cl.
*A61B 17/70* (2006.01)

(52) U.S. Cl.
CPC ......... *A61B 17/7083* (2013.01); *A61B 17/7002* (2013.01); *A61B 17/7004* (2013.01); *A61B 17/7011* (2013.01); *A61B 17/7089* (2013.01); *A61B 17/701* (2013.01)

(58) Field of Classification Search
CPC ........... A61B 17/7002; A61B 17/7011; A61B 17/7083; A61B 17/7089
See application file for complete search history.

(56) References Cited

U.S. PATENT DOCUMENTS

| | | | |
|---|---|---|---|
| 6,530,929 B1 * | 3/2003 | Justis | A61B 17/1671 606/103 |
| 7,066,937 B2 | 6/2006 | Shluzas | |
| 7,188,626 B2 * | 3/2007 | Foley | A61B 17/1671 128/898 |
| 7,520,879 B2 * | 4/2009 | Justis | A61B 17/7002 606/86 A |
| 7,758,617 B2 * | 7/2010 | Iott | A61B 17/701 606/246 |
| 7,892,239 B2 * | 2/2011 | Warnick | A61F 2/4465 606/279 |
| 8,157,845 B2 * | 4/2012 | Warnick | A61F 2/4455 606/279 |
| D722,698 S * | 2/2015 | Frankel | D24/171 |
| 2005/0277934 A1 * | 12/2005 | Vardiman | A61B 17/7083 606/914 |
| 2006/0247630 A1 * | 11/2006 | Iott | A61B 17/701 606/86 A |
| 2007/0078460 A1 * | 4/2007 | Frigg | A61B 17/7002 606/86 A |
| 2007/0225808 A1 * | 9/2007 | Warnick | A61F 2/4465 623/17.11 |
| 2008/0009880 A1 * | 1/2008 | Warnick | A61F 2/4455 606/99 |
| 2008/0045956 A1 * | 2/2008 | Songer | A61B 17/7002 606/86 A |
| 2008/0077138 A1 * | 3/2008 | Cohen | A61B 17/7083 606/86 A |

FOREIGN PATENT DOCUMENTS

EP 1221901 2/2007
WO WO2007087516 8/2007

* cited by examiner

*Primary Examiner* — Ellen C Hammond
(74) *Attorney, Agent, or Firm* — McHale & Slavin, P.A.

(57) ABSTRACT

The present invention provides for a bone fixation device, an implantation instrument, and system which are useful in bone fixation surgeries. The bone fixation device of the instant invention allows the surgeon the ability to navigate the rod while being inserted into a pedicle screw assembly through a non-linear pathway by incrementally changing the direction of travel as desired.

18 Claims, 5 Drawing Sheets

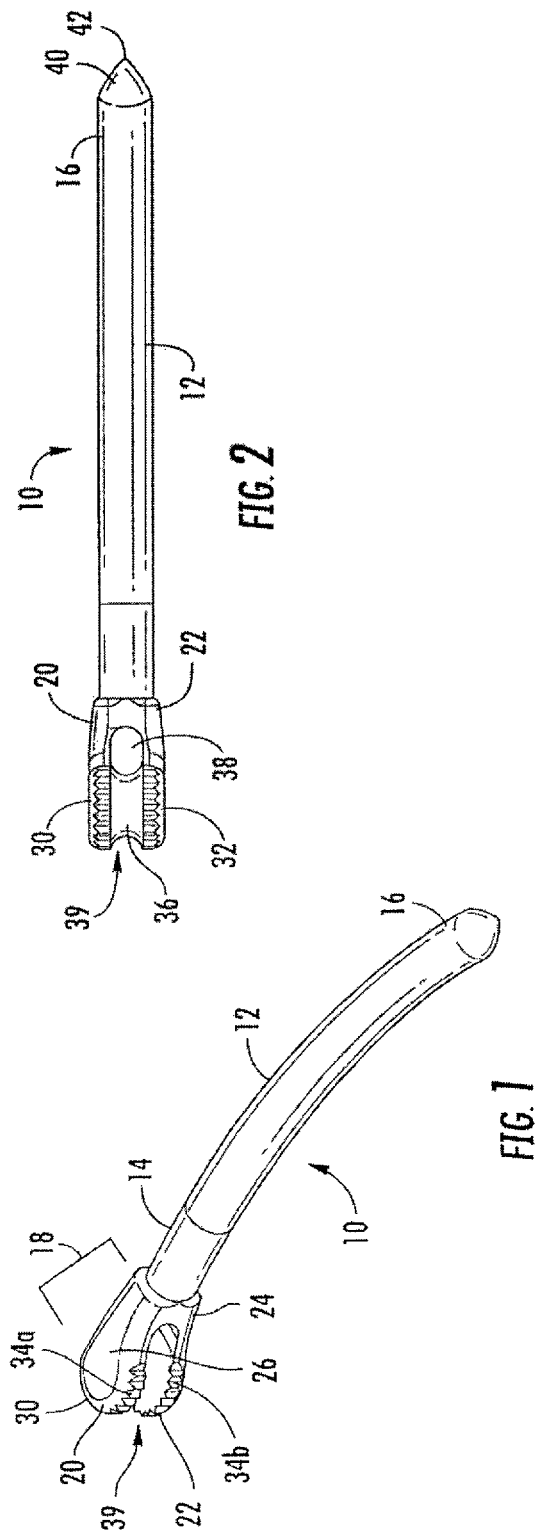
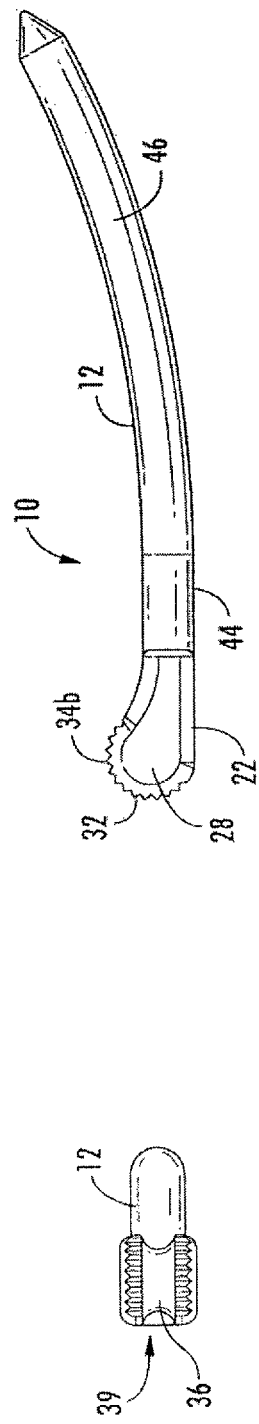

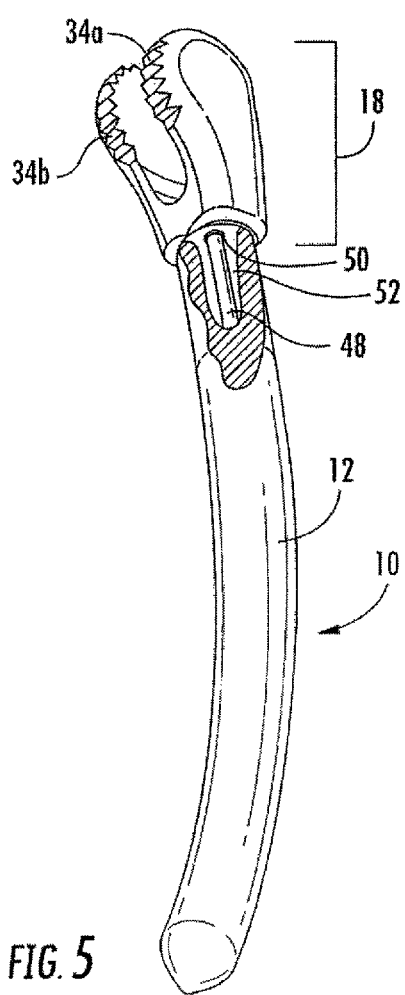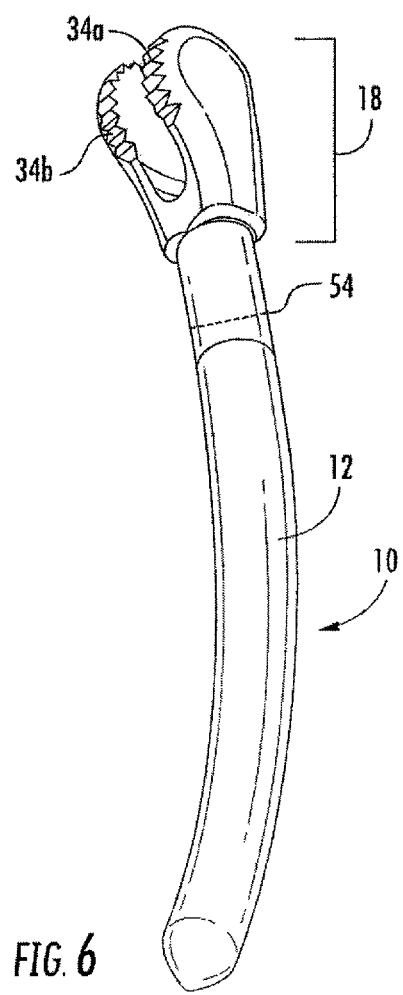

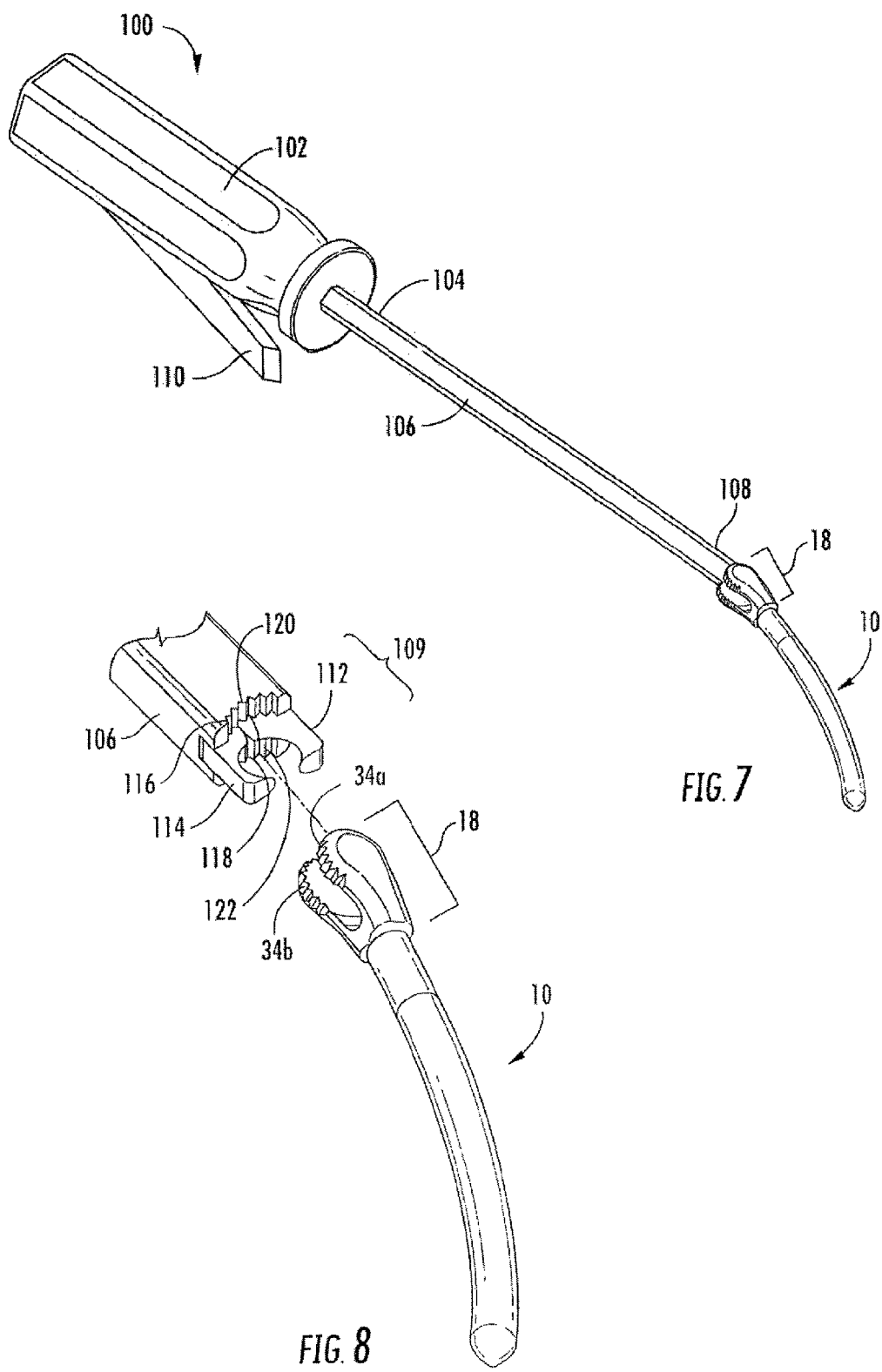

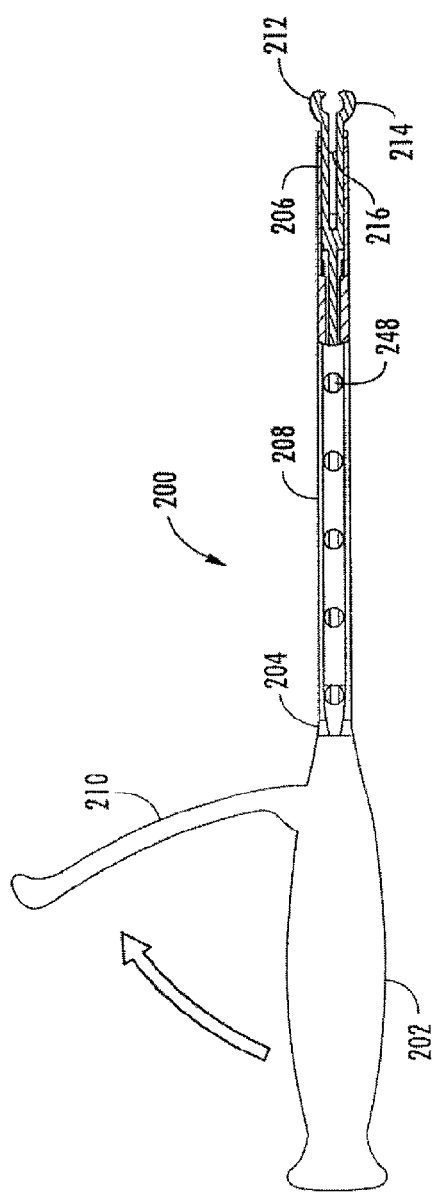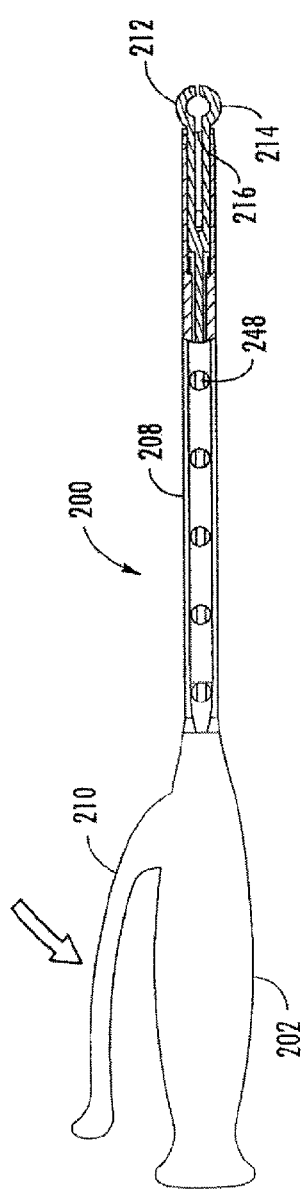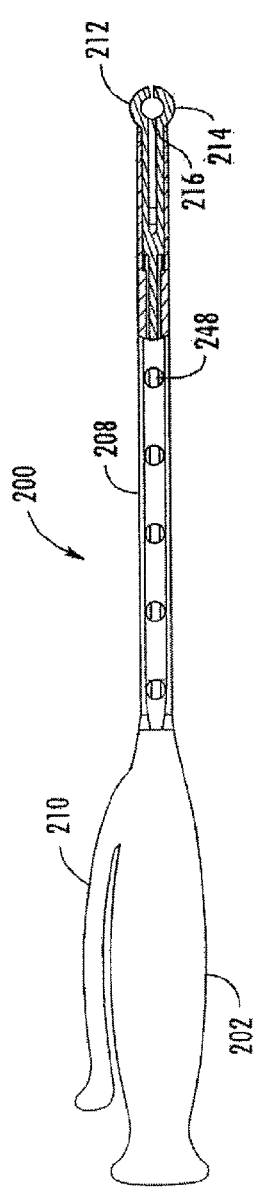

BONE FIXATION ROD AND IMPLANTATION DEVICE FOR INSERTION THEREOF

CROSS REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 13/107,189, filed May 13, 2011, entitled "Bone Fixation Rod And Implantation Device For Insertion Thereof", which claims priority under 35 USC 119(e) to the U.S. Provisional Patent Application No. 61/334,643, filed May 14, 2010, entitled, "Bone Fixation Rod And Implantation Device For Insertion Thereof", which is now incorporated herein by reference.

FIELD OF THE INVENTION

The instant invention relates to surgical instruments useful in bone fixation procedures and methods of use thereof; and more particularly to a bone fixation rod, such as a spinal rod, and an implantation instrument used for insertion into a plurality of pedicle screws for alignment purposes during spinal procedures.

BACKGROUND OF THE INVENTION

The central nervous system is a vital part of the human physiology that coordinates human activity. It is primarily made up of the brain and the spinal chord. The spinal chord is made up of a bundle of nerve tissue which originates in the brain and branches out to various parts of the body, acting as a conduit to communicate neuronal signals from the brain to the rest of the body, including motor control and sensations. Protecting the spinal chord is the spinal, or vertebral, column. Anatomically, the spinal column is made up of several regions, including the cervical, thoracic, lumbar and sacral regions. The cervical spine is made up of seven vertebrae and functions to support the weight of the head. The thoracic spine is made up of 12 vertebrae and functions to protect the organs located within the chest. Five vertebrae make up the lumbar spine. The lumbar spine contains the largest vertebra and functions as the main weight bearing portion of the spine. Located at the base of the spine is the five fused vertebrae known as the sacrum. The coccyx sits at the base of the spinal column and consists of four fused vertebrae.

Each of the vertebrae associated with the various spinal chord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal chords, it is not uncommon for individuals to suffer some type of spinal ailment, including spondylolisthesis, scoliosis, or spinal fractures. One of the more common disorders associated with the spinal chord is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. For example, disc herniation is a condition in which the disc substance bulges from the disc space between the two vertebrae bodies. It is the bulging of the disc material which causes impingement on the nerves, manifesting in pain to the patient. For most patients, rest and administration of pain and anti-inflammatory medications alleviates the problem. However, in severe cases, cases which have developed into spinal instability or severe disc degeneration, the damaged disc material between the vertebral bodies is removed and replaced with spinal stabilization implants. Restoration to the normal height allows the pressure on the nerve roots to be relieved.

There are many different approaches taken to alleviate or minimize severe spinal disorders. One surgical procedure commonly used is a spinal fusion technique. Several surgical approaches have been developed over the years, and include the Posterior Lumbar Interbody Fusion (PLIF) procedure which utilizes a posterior approach to access the patient's vertebrae or disc space, the Transforaminal Lumbar Interbody Fusion (TLIF) procedure which utilizes a posterior and lateral approach to access the patient's vertebrae or disc space, and the Anterior Lumbar Interbody Fusion (ALIF) which utilizes an anterior approach to access the patient's vertebrae or disc space. Using any of these surgical procedures, the patient undergoes spinal fusion surgery in which two or more vertebrae are linked or fused together through the use of a bone spacing device and/or use of bone grafts. The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal spacers and/or bone grafts have been inserted, a surgeon places the pedicle screws into a portion of the spinal vertebrae and attaches either rods or plates to the screws as a means for stabilization while the bones fuse. Currently available systems for inserting the rods into pedicle screws can be difficult, particularly in light of the fact that surgeons installing these rods often work in narrow surgical fields. Moreover, since patients can vary with respect to their internal anatomy resulting in varying curvatures of the spine, a surgeon may not always have a linear path or may have anatomical structures that must be maneuvered around in order to properly insert the surgical rods into the pedicle screw assemblies. In addition to requiring surgical skill, difficulty in placing the rods correctly into the pedicle screws can result in unnecessary increases in the time it takes a surgeon to complete the surgical procedure. Prolonged surgery times increase the risk to the patient. More importantly, improperly aligning the rods and pedicle screw assemblies often results in complications for the patient and requires corrective surgical procedures.

There exists, therefore, a need for an improved bone fixation rod and bone fixation implantation instrument that can be used by a surgeon to easily and safely insert the bone fixation rod to a plurality of embers of a bone fixation system, such as pedicle screws which have been inserted into various bone structures.

DESCRIPTION OF THE PRIOR ART

U.S. Pat. No. 6,530,929 discloses an installation instrument for placement of a brace or rod into pedicle screws. The instrument is mounted to anchors secured to the pedicle screws utilizing extensions coupled to the anchors. The instrument is movable with respect to the anchors to position a brace in a position more proximate the anchors. The brace can be inserted into the pedicle screws and manipulated away from the installation instrument utilizing thumb screw. However, a disadvantage associated with the installation instrument for placement of a brace or rod into pedicle screws described therein is that the brace can not be rotated about its longitudinal axis.

U.S. Pat. No. 7,188,626 discloses methods and instruments for placing a brace or connecting element into a plurality of anchors or pedicle screws similar to U.S. Pat. No. 6,530,929. Insertion of the connecting elements is accomplished by a linear insertion method, therefore failing to teach a connecting element that can to be rotated about its longitudinal axis.

U.S. Pat. No. 7,520,879 discloses a device for positioning a connecting element adjacent the spinal column using minimally invasive procedures. An inserter instrument guides the connecting element from a location remote from one or more anchors to a location proximate to the one or more anchors. The extensions are mountable to anchors, and the inserter instrument is mountable to the connecting element for positioning the connecting element adjacent the anchors in a minimally invasive procedure. The inserter instrument does not have to be mounted to the anchors or to the anchor extensions, and are operable independently to position the connecting element into the patient along a minimally invasive insertion path from a location remote from the anchor extensions. While the inserter instrument can rotate the connecting element along its longitudinal axis, it can not be repositioned on the connecting element to gradually rotate the connecting element in a given direction. Moreover, it cannot be rotated about an axis normal to its longitudinal axis.

U.S. Publication No. 2007/0078460 discloses a method and instrumentation for performing spinal fixation surgery. A first incision is made through the skin and a passageway is created to the spine. A screw is inserted through the passageway and into a vertebra. The screw has a head portion including a channel. An insertion guide is operably connected to the screw. Additional screws may each be inserted through separate incisions or through the first incision. Insertion guides may be operably connected to a head portion of each screw. A sleeve may be positioned into one insertion guide in a first position to guide a rod through at least one other insertion guide. The sleeve is rotated to a second position to allow the rod to move down the slots of the insertion guides and into the head portion of the screw. Additionally a holding instrument can be employed to position a rod. Two types of connections between the holding instrument and the rod are described. These connections permit the rotation of the rod about its longitudinal axis, but fail to teach a rod which can be repositioned on the connecting element to gradually rotate the connecting element in a given direction.

U.S. Published Application No. 2005/0277934 discloses a minimally invasive spinal fixation system used for spinal arthrodesis or motion preservation spinal repair. The system includes a plurality of pedicle screws and an attachment assembly for connecting the pedicle screws. The attachment assembly includes a connector for attaching to the first screw and second screw, and a removable guide for percutaneously attaching the connector to the first screw and second screw. The removable guide includes a number of different embodiments for connecting the attachment assembly to the connector. A snap type lock is used to secure the attachment to the connector. While this does permit the connector to be repositioned by rotating it about its longitudinal axis, the repositioning can occur at only 90 degree increments. Moreover, it can not be rotated about an axis normal to the longitudinal axis of the connector.

U.S. Pat. No. 7,892,239, and U.S. Published Application Nos. 2007/0225808 and 2008/0009880 describe a system and a method for pivotably inserting an interbody spacer device into a surgical site. The system includes an interbody spacer and an insertion instrument with a pivotable element configured to manipulate an interbody spacer. A plurality of teeth is formed on at least one end of the spacer and matching teeth are formed on an insertion instrument. An exemplary insertion instrument includes an expandable tip configured to be inserted and mated with a gap within an interbody spacer to aid in selective retention and manipulation of the interbody spacer.

Therefore, what is needed is a bone fixation rod which does not require a surgeon to use a predetermined, fixed linear pathway when attempting to insert the rod into a plurality of pedicle screw assemblies. A bone fixation device, and instrumentation for insertion, which allows the surgeon the ability to navigate the rod while being inserted into a bone fixation system, such as a pedicle screw assembly, through a non-linear pathway by incrementally changing the direction of travel is also desired.

SUMMARY OF THE INVENTION

The present invention provides for a bone fixation rod, and an implantation instrument for delivery of the bone fixation rod to a plurality of pedicle screws, which is useful in bone fixation surgeries. The bone fixation device as described herein provides a surgeon with a device that can easily and safely be inserted into a plurality of pedicle screws for alignment purposes during orthopedic procedures without the need for using a predetermined insertion pathway.

As such, the bone fixation rod comprises a main body having a proximate end and a distal end. Positioned at the proximate end is an implantation instrument receiving member. The implantation instrument receiving member has two upwardly shaped arms which connect at a base to form a generally U-shaped configuration. A portion of the two upwardly shaped arms contain partially circular surfaces. The implantation instrument receiving member is constructed such that cut into a portion of the outer surface or circumference of the partially circular surface are ridges or teeth. A contoured cylindrical member links the upper portions of the upwardly shaped arms, thereby forming a cavity. The distal end of the bone fixation rod can be constructed to contain a tapered portion. The tapered portion may end with a pointed tip which aids the surgeon by providing a mechanism for pushing tissue to the side as the bone fixation device is maneuvered to its final resting position within a pedicle screw. The main body has a generally cylindrical, elongated shape containing a linear portion and/or a portion containing curvature.

The bone fixation rod is designed to be engagable with an implantation instrument. A particular embodiment of an implantation instrument of the instant invention includes a device having a handle, a shaft, and a bone fixation rod engaging portion positioned at the distal end of the implantation instrument. Engagement of the bone fixation rod to the implantation instrument can be accomplished by use of opposing jaws which are part of the bone fixation rod engaging portion and positioned at the distal end of the instrument. A lever located on the handle is used to provide the user a mechanism for opening the opposing jaws. The opening of the opposing jaws allows for insertion and engagement with the implantation instrument receiving area of the bone fixation rod. In this position, despite being engaged by the opposing jaws, the bone fixation device is capable of rotation without becoming disengaged from the implantation instrument. Engaging the lever to a third position retracts the jaws into the shaft. In this position, the bone fixation rod is firmly held in place and can not pivot relative to the opposing jaws. By disengaging and engaging the lever such that the opposing jaws toggle between the three positions, the user can navigate the rod while it is inserted into a pedicle screw assembly without being restricted to a predetermined, linear pathway. The implantation device also provides the surgeon with the ability to maneuver the bone fixation rod in a non-linear fashion around tissue structures by incrementally changing the direction of travel until the rod reaches its final destination.

Accordingly, it is a primary objective of the instant invention to provide an improved bone fixation rod which is useful in bone fixation surgeries.

It is a further objective of the instant invention to provide a bone fixation rod constructed to provide for angular adjustment during insertion.

It is yet another objective of the instant invention to provide a bone fixation rod which can be locked in place in order to maintain an angular position.

It is a still further objective of the invention to provide a bone fixation rod which allows a surgeon the ability to navigate the rod while being inserted into a pedicle screw assembly through a non-linear pathway by incrementally changing the direction of the rod until it reaches its final destination.

It is yet another objective of the instant invention to provide a bone fixation rod which does not require a surgeon to use a predetermined, fixed linear pathway when attempting to insert the rod into a plurality of pedicle screw assemblies.

It is a still further objective of the invention to provide an implantation instrument that can engage the bone fixation device as described herein.

It is a further objective of the instant invention to provide for an implantation instrument that can make incremental adjustments to the bone fixation rod as the rod is being inserted into a pedicle screw assembly.

It is yet another objective of the instant invention to provide for an implantation instrument that can maintain the angular positioning of the bone fixation rod as the rod is inserted into a pedicle screw assembly.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1 is a prospective view of the bone fixation rod of the instant invention;

FIG. 2 is a side view of the bone fixation rod of the instant invention;

FIG. 3 is a longitudinal cross sectional view of the bone fixation rod of the instant invention;

FIG. 4 is a front plan view of the bone fixation rod of the instant invention;

FIG. 5 is a prospective view of an alternative embodiment of the bone fixation device, showing a partial cut view of a separable implantation receiving member;

FIG. 6 is a prospective view of an alternative embodiment of the bone fixation device, showing the separation features positioned along the main body;

FIG. 7 illustrates the attachment of the bone fixation rod of the instant invention to an implantation instrument;

FIG. 8 illustrates the distal end of the bone fixation rod illustrated in FIG. 5;

FIG. 9A represents an alternative embodiment of an implantation instrument shown with a lever in a first position which corresponds to opposing jaws in an open position;

FIG. 9B illustrates the implantation instrument of FIG. 9A with the lever in a second position. Although not illustrated in the figure, this position allows the opposing jaws to engage the bone fixation device;

FIG. 9C illustrates the implantation instrument of FIG. 9A with the lever in a third position in which the opposing jaws have been closed. Although not illustrated in the figure, this position allows the teeth associated with two upwardly shaped arms of the implantation instrument receiving member of the bone fixation rod to engage the teeth area of the implantation instrument, thereby locking the rod in place;

DETAILED DESCRIPTION OF THE INVENTION

Figure 10:
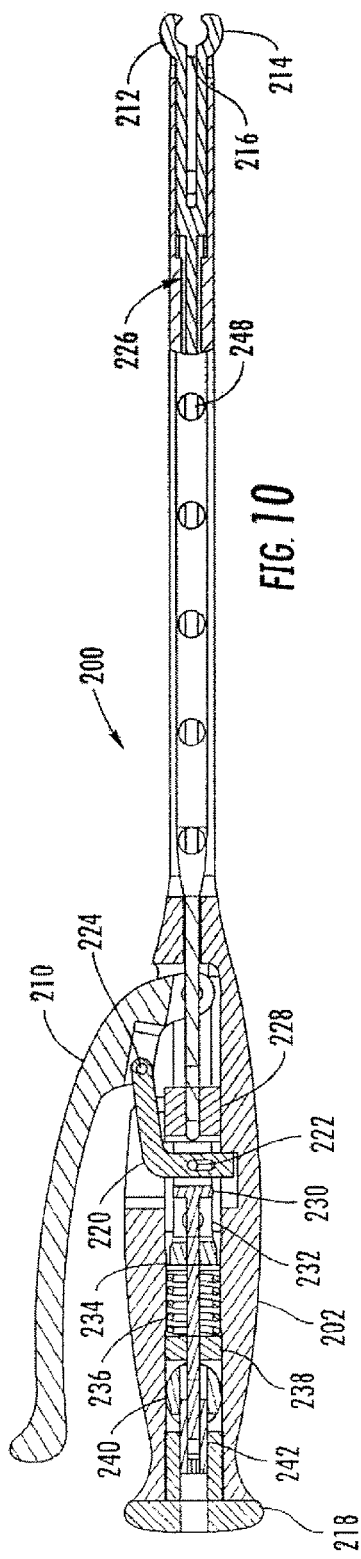
FIG. 10 is a longitudinal cross sectional view of the implantation instrument illustrated in FIGS. 9A-9C.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring now to FIGS. 1-4, a bone fixation device will now be described. While the bone fixation device will be described as a spinal rod associated with a pedicle screw assembly of a spinal fixation device, one of skill in the art would recognize that such instrumentation is not limited to spinal fixation devices and may be applied to other applications and other bone fixation systems as well. The unique aspect of the bone fixation device of the instant invention is that it is constructed to provide for angular adjustment during insertion and can be locked in place in order to maintain an angular position. In addition, the bone fixation device of the instant invention gives the user the ability to infinitely reposition an implantation instrument with respect to the bone fixation device, thereby providing an advantage over the prior art rods by permitting the user to make very small, incremental adjustments to the bone fixation device as the device is being inserted.

As used herein, the term "proximate end" defines the end closest to the user, i.e. surgeon, when in use.

As used herein, the "distal end" is defined as the end located farthest from the user and closest to the bone anchor device, i.e. a pedicle screw, when in use.

As used herein, "pedicle screw" or "pedicle screw assembly" is used to describe commonly used orthopedic or spinal surgical instrumentation, individually or as a unit, such as described in U.S. Pat. No. 7,066,937. While many embodiments of a pedicle screw exist commercially, the typical pedicle screw assembly consists generally of the pedicle screw containing a threaded portion which is inserted into a bone or spinal vertebrae. Connected to the screw is a housing unit having upwardly shaped arms which form a U-shape unit. The housing unit is generally constructed to receive a longitudinal or spinal rod. The longitudinal or spinal rod is set to the housing through use of a set screw which can be designed to screw into a threaded portion of the housing to lock the rod into place. This general construction scheme allows the surgeon to connect and secure adjacent bones together through use of the pedicle screw assembly, thereby providing stability temporarily until the bones heal or, if needed, permanently.

FIGS. 1 and 2 illustrate the bone fixation device 10 of the instant invention comprising a main body 12, a proximate end 14 and a distal end 16. Positioned at the proximate end 14 is an implantation instrument receiving member 18 constructed to provide angular adjustment to the rod during insertion. The implantation instrument receiving member 18 has two upwardly shaped arms 20 and 22 connected at a base 24 to form a generally U-shaped configuration. The two upwardly shaped arms 20 and 22 have a flat surface 26 and 28 (FIG. 3), respectively, and a partially circular surface 30 and 32, respectively. The implantation instrument receiving member 18 contains engagement members, illustrated herein as a plurality of ridges or teeth, 34a, associated with the upwardly shaped arm 20, and 34b, associated with the upwardly shaped arm 22, cut into a portion of the outer surface or circumference of the partially circular surfaces 30 and 32. The plurality of teeth disposed about the outer surface or circumference allow for an implantation instrument to firmly grip the implantation instrument member 18 and aid in the manipulation of the spinal rod 10 during insertion into the pedicle screws. In addition to the plurality of teeth 34a and 34b, disposed on the outer surface or circumference of one or both of the partially circular surfaces 30 and 32 can be other frictional features such as protruding features, materials, or rough surfaces to pivotably direct the spinal rod 10 during implantation into the pedicle screws. A contoured cylindrical member 36 links the upwardly shaped arms 20 and 22, see FIG. 2 and FIG. 4, and forms a cavity 38. The cylindrical member and the cavity 38 faun an implantation instrument receiving area 39 which couples the instrument receiving member 18 to a first portion of an implantation instrument. The distal end 16 contains a tapered portion 40 with or without a pointed tip 42. While FIG. 2 illustrates a pointed tapered end, the distal end could be any shape including round, oval, square, polygonal, or the like.

The main body 12, as illustrated in FIG. 3, is shown as a cylindrical, elongated member containing a portion which is generally linear 44, i.e., having no or little curvature, and a portion containing curvature 46. Because the main body 12 is illustrated as a generally cylindrical body, it has a rounded diameter. The diameter size can be varied depending on the need of the user. However, it is not necessary that the main body retain the round-shaped diameter. The main body 12 can be constructed to contain curvature in varying degrees. The length of the bone fixation device 10 can be varied depending on the need of the user. The main body 12 can also be constructed without curvature. The bone fixation rod 10 is preferably made of surgical grade stainless steel, but can be made of other materials such as titanium, aluminum, an alloy, carbon fiber composite, or a polymer, such as polyvinyl chloride (PVC), polyethylene, polyesters of various sorts, polycarbonate, Teflon coated metal, polyetheretherketone (PEEK), or ultra high molecular weight polyethylene (UHMWPE). Additionally, the bone fixation rod 10 can be made to be radiolucent or radioopaque.

The implantation instrument receiving member 18 may be made of the same material as the main body 12 and may be integrally formed with the main body 12. Alternatively, implantation instrument receiving member 18 may be constructed from a different material than that used for the main body. The implantation instrument receiving member 18 may be designed so that once the main body 12 is in its proper alignment, the implantation instrument receiving member 18 can be removable. Such functionality can be accomplished in a variety of ways. FIG. 5 illustrates an alternative embodiment of the bone fixation device 10. As shown in the partial cut out view, the bone fixation device comprises an implantation instrument receiving member 18 containing a protruding member 48 positioned at the distal end 50. The protruding member 48 is sized and shaped to be received by a hollowed area 52 positioned within the main body 12. In this manner, the protruding member 48 is inserted, such as through press fit manner, into the main body through the hollowed area 52. The fitting can be designed such that the implantation instrument receiving member 18 remains in place during the insertion process, but can be removed by adding a force that snaps it off the main body 12. As an alternative to securing the implantation instrument receiving member 18 to the main body through press fitting, a tangent pin may be inserted into the main body 12, extending through the protruding member 48. Removal of the implantation instrument receiving member 18 is accomplished by removal of the pin and lifting the implantation instrument receiving member 18 from the main body 12. The bone fixation device 10 may have an implantation instrument receiving member 18 which is secured to the main body 12 through a collar or use of a clip (not illustrated). As needed, the collar or clip can be removed and the implantation instrument receiving member 18 can be retrieved. Referring to FIG. 6, the bone fixation device 10 may include one or more separating features 54, such as perforations, laser spots, fracture initiating lines, a groove which has a depth corresponding to a pre-determined magnitude of a fracture torque or other force, or other mechanisms which allow the user to separate the user implantation instrument receiving member 18 from the main body 12. Preferably, the separating features 54 allow separation between the two sections when a predetermined force or torque is applied to the area, thereby snapping the implantation instrument receiving member 18 off the main body 12. The implantation instrument receiving member 18 may be made of a bioabsorbable material that is designed to safely degrade over time within the body. The implantation instrument receiving member 18 may additionally be made to be frangible and/or of a bioabsorbable material which dissolves and is absorbed in the body, such as through the use of bioabsorbable polymers including but not limited to polyglycolide, polyglycolide-co-rimethethylene carbonate, polyglyconate, poly-DL-lactide co-glycolide, poly-DL-lactide, polyDl-lactide-co-L-lactide, poly-L-lactide, or other bioabsorbable materials known to one of skill in the art.

Insertion of the bone fixation rod 10 is accomplished by use of an implantation instrument. FIG. 7 illustrates the attachment of the bone fixation rod 10 to an implantation instrument 100. The implantation instrument 100 contains a handle 102 positioned at the proximate end 104. Extending from the handle 102 is a substantially cylindrical elongated shaft 106. At the distal end 108 of the implantation instrument 100 is a bone fixation rod grasping region 109 which is constructed and arranged to grasp the bone fixation rod 10, see FIG. 8. The handle 102 contains an actuating device, such as a lever 110, mechanically and pivotably connected to the bone fixation grasping region through interior mechanical mechanisms (not illustrated). Manipulation of the lever allows the user to engage the implantation instrument 100 with the implantation instrument receiving member 18 of the bone fixation device 10. As illustrated in FIG. 8, the bone fixation rod grasping region contains opposing jaws 112 and 114 and concave surfaces 116 and 118. The concave surfaces each contain a plurality of ridges or teeth 120 and 122 or other frictional features designed to engage the plurality of teeth or ridges on the bone fixation device 10. In use, the opposing jaws 112 and 114 engage the contoured cylindrical member 36 and couple and hold the bone fixation device 10 through the cavity 38. The ridges or teeth 34a and 34b which are cut into a portion of the outer surface of the partially circular surface 30 and 32 of the implantation instrument receiving member 18 are received by the plurality of teeth 120 and 122 of the implantation instrument 100.

Figure 12:
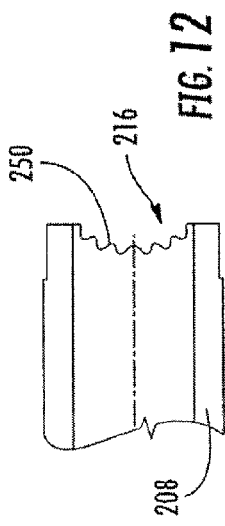
FIG. 12 illustrates a blown-up view of the teeth receiving area positioned at the distal end of the implantation instrument as shown in FIG. 10 without the opposing jaws.

FIGS. 9A-9C illustrate an alternative embodiment of the implantation instrument. The implantation instrument 200 provides the user the ability to engage the bone fixation rod 10 in a similar manner as described before. The implantation device 200 contains a handle 202 positioned at the proximate end 204. Extending from the handle 202 towards the distal end 206 is a shaft 208. The handle 202 includes a lever 210, which when manipulated by the user allows opposing jaws 212 and 214 to open and close, thereby engaging the proximal end of the bone fixation rod 10. FIG. 9A illustrates the lever in a first open position. This position is obtained by pulling the lever away from the handle, see arrow, causing the opposing jaws 212 and 214 to extend from the shaft of the body and to open by moving in opposite directions. While in this position, the proximal end of the bone fixation rod 10 may be inserted into the implantation instrument through engaging the cylindrical member 36 and alignment with the cavity 38. FIG. 9B illustrates the lever 210 in a second position, obtained by manipulating the lever in a direction towards the handle 202, see arrow. When the user further engages the lever to a position closer to the handle, the opposing jaws are drawn closer. As the opposing jaws move inwardly, they engage the bone fixation rod 10 (not shown) by clamping onto cylindrical member 36 which links the upwardly shaped arms 20 and 22 through the cavity 38. In the second position, the bone fixation rod 10 is permitted to rotate about its longitudinal axis and to rotate about an axis that is normal to its longitudinal axis. FIG. 9C illustrates the lever 210 in a third position. As the lever 210 is drawn closer to the handle, the opposing jaws are retracted inwardly. In this position, the teeth 34a and 34b of the bone fixation rod 10 engage the teeth 250 (see FIG. 12, a blown up view of the distal end of the shaft 208 without the opposing jaws) of the teeth receiving area 216 of the implantation instrument 200 which are positioned at the distal end of the device, in a retracted position relative to the opposing jaws 212 and 214. Once the lever has been placed in the third position, the bone fixation rod 10 is locked in place.

Figure 11:
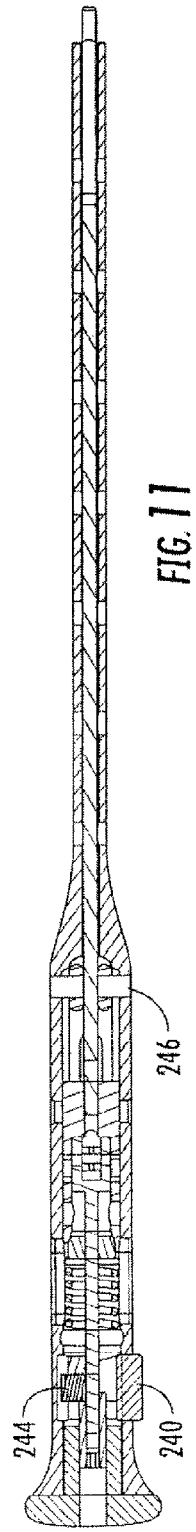
FIG. 11 is longitudinal cross sectional top view of the implantation device illustrated in FIGS. 9A-9C.

FIGS. 10 and 11 are cross sectional views of the implantation instrument 200. At the most proximate end of the handle 202 is a cap 218. As described previously, the lever 210 provides the user the ability to manipulate the opposing jaws 212 and 214. The lever 210 is connected to a linking member 220 through a link pin 222 and a lever pin 224. Manipulation of lever 210 causes the draw rod 226 to move in a linear forward/backwards motion causing the opposing jaws 212 and 214 to open (forward motion) or close (backward/retracting motion). The opening and closing of the jaws is accomplished by mechanical interconnection of various elements housed within the handle and the shaft, including, but not limited to, the draw rod 226, a slack cylinder 228, core element 230, washers stacked in series 232, a slack stop 234, a return spring 236, a return stop 238, a release button 240, a catch nut 242, a button spring 244 and a cross pin 246. Positioned throughout the shaft 208 are apertures 248 which can be utilized in sanitization techniques, such as autoclaving, to sterilize the instrument.

The present exemplary device and system provide for a pivotable bone fixation device that provides the user the ability to insert the bone fixation device in a non-linear path. The implantation instrument is designed to lock the bone fixation rod at multiple angles to allow for the bone fixation rod to be pivoted in increments if the instrument rotation is restricted such that the instrument can only be rotated less than the total rotation implemented to position the rod. Moreover, the bone fixation device and system provide the user the ability to easily load, unload, and manipulate the spinal rod angle. Because of the unique design as described herein, the bone fixation rod can be safely and accurately pivoted without disengaging from the implantation instrument, eliminating the additional need for other instruments, such as pushers or persuaders.

An exemplary method of using the bone fixation device 10 may include engaging of the bone fixation device 10 with the implantation instrument 200 prior to inserting the bone fixation device into one or more members of a bone fixation system, such as a plurality of pedicle screws. To engage the bone fixation device 10, the lever 210 is moved to a first position. In this position, the draw rod 226 located in the shaft of the implantation device 200 extends outwardly, opening the retractable jaws 212 and 214. Pushing the lever 210 to the second position allows the bone fixation device 10 to be coupled to the insertion instrument 100 through engagement of the retractable jaws 212 and 214 with the cylindrical portion 36 of the implantation instrument receiving member 18 at the cavity 38. The engagement at this position allows the bone fixation device 10 to be rotatable. The bone fixation device is then orientated to a desired angle and locked in place by moving the lever 210 to a third position. In the third position, the draw rod 226 located in the shaft of the insertion device is pulled towards the proximal end causing the engaging members 34a and 34b of the implantation instrument receiving member 18 to engage the engaging members 216 of the insertion instrument, thereby restraining the bone fixation device 10 from pivoting with respect to the instrument. Once in the proper orientation, the bone fixation device can be inserted into the body and aligned with pedicle screws which have been inserted into the pedicle bone on the back of the spinal column. The device 10 is moved until it can no longer follow a linear path. At that time, should the bone fixation device 10 not be completely placed within all the pedicle screws, the bone fixation device may be pivoted to provide further insertion along a redirected pathway. To pivot the bone fixation device about the end of the implantation instrument 200, the user redirects the lever 210 to the second position. This action disengages the coupling of the engagement members 34a and 34b of the implantation instrument receiving member 18 with the engagement member of the insertion instrument 216. The bone fixation device 10 remains pivotably coupled to the implantation instrument through engagement of the retractable jaws 212 and 214. The implantation instrument can, therefore, be pivoted with respect to the bone fixation device 10 and returned to the locked position by engaging the lever. The lever 210 is then engaged back to the third position, locking the bone fixation device 10 in place. By disengaging and engaging the lever such that the opposing jaws toggle between the three positions, the user can navigate the bone fixation device 10 while it is inserted into a pedicle screw assembly without being restricted to a predetermined, linear pathway. The implantation device also provides the user with the ability to maneuver the bone fixation rod in a non-linear fashion around tissue structures by incrementally changing the direction of travel until the bone fixation device reaches its final destination.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of traversing a pathway with a connecting member for bone implants comprising:
providing an implant connecting member in the form of a bone fixation rod, said bone fixation rod including a main body having a proximate end, a center portion and a distal end, said proximate end including at least one arm supporting a transversely secured cylindrical portion, a side surface of said at least one arm including a circular surface, said circular surface having a plurality of frictional engagement features extending thereabout;
providing an implantation instrument for delivery of the implant connecting member, said implantation instrument including a handle positioned at a proximate end thereof and a grasping region at the distal end thereof, said grasping region including at least one jaw member for rotatable cooperation with said cylindrical portion and at least one concave surface for frictional cooperation with said frictional engagement features,
said implantation instrument having a first open position whereby said at least one jaw member is extended away from a body of said implantation instrument whereby said cylindrical surface is positionable within said at least one jaw member,
said implantation instrument having a third position for said at least one jaw member whereby said circular surface having a plurality of frictional engagement features engages said concave surface whereby said bone fixation rod is fixed with respect to said implantation instrument,
said implantation instrument having a mechanical manipulator for movement of said at least one jaw member between said first and said third positions, whereby said bone fixation rod is restrained from pivoting with respect to said insertion instrument;
attaching said implantation instrument to said implant connecting member; and
inserting said implant connecting member into a plurality of pedicle screws.

2. The method of traversing a pathway with a connecting member for bone implants of claim 1, wherein said implantation instrument includes a second position for said at least one jaw member whereby said bone fixation rod is secured to said implantation instrument so that said bone fixation rod is permitted to rotate about its longitudinal axis and to rotate about an axis that is normal to its longitudinal axis, whereby said bone fixation rod can be pivoted with respect to said implantation instrument without disengaging said bone fixation rod from the implantation instrument.

3. The method of traversing a pathway with a connecting member for bone implants of claim 2, wherein said mechanical manipulator is positioned at said proximal end of said implantation instrument, said mechanical manipulator secured to a draw rod, said draw rod secured to said at least one jaw member for selective movement of said at least one jaw member between said first, said second and said third positions.

4. The method of traversing a pathway with a connecting member for bone implants of claim 3, wherein said mechanical manipulator is manually operable to move said at least one jaw member between said first, said second and said third positions as desired during insertion of said bone fixation rod into an animal in vivo.

5. The method of traversing a pathway with a connecting member for bone implants of claim 3, wherein said implantation instrument is provided with two jaw members positioned to oppose each other.

6. The method of traversing a pathway with a connecting member for bone implants of claim 3, wherein said implantation instrument includes a tubular central portion, said draw rod extending through said tubular portion for operation of said at least one jaw member.

7. The method of traversing a pathway with a connecting member for bone implants of claim 2, wherein said proximate end of said bone fixation rod includes two arms supporting the transversely secured cylindrical portion at each distal end thereof, a side surface of each said two arms including a circular surface, each said circular surface having a plurality of frictional engagement features extending thereabout.

8. The method of traversing a pathway with a connecting member for bone implants of claim 1, wherein said frictionally engaging features on said circular surface of said fixation rod are teeth, said at least one concave surface of said implantation instrument including teeth having a substantially conjugate profile with respect to said bone fixation rod teeth.

9. The method of traversing a pathway with a connecting member for bone implants of claim 1, wherein said distal end of said fixation rod is conical in shape.

10. The method of traversing a pathway with a connecting member for bone implants of claim 1, wherein said center portion of said bone fixation rod is an elongated cylinder having no curvature along the longitudinal length thereof.

11. The method of traversing a pathway with a connecting member for bone implants of claim 1, wherein said center portion of said bone fixation rod is an elongated cylinder having curvature along the longitudinal length thereof.

12. The method of traversing a pathway with a connecting member for bone implants of claim 1, wherein said proximate end of said bone fixation rod is constructed from a different material than said center portion and said distal end.

13. The method of traversing a pathway with a connecting member for bone implants of claim 12, wherein said proximate end is removable from said center portion and said distal end.

14. The method of traversing a pathway with a connecting member for bone implants of claim 12, wherein said proximate end is constructed from a bioresorbable material.

15. The method of traversing a pathway with a connecting member for bone implants of claim 1, wherein said bone fixation rod includes one or more separating features, whereby applying a predetermined force to said separating features removes said proximal end from said center portion and said distal end.

16. The method of traversing a pathway with a connecting member for bone implants of claim 15, wherein said proximate end is frangible from said center portion and said distal end.

17. The method of traversing a pathway with a connecting member for bone implants of claim 15, wherein said proximal end of said bone fixation rod contains a protruding member sized and shaped to fit within a hollow lumen within said center portion.

18. The method of traversing a pathway with a connecting member for bone implants of claim 17, wherein said proximal end is further secured to said center portion through a tangent pin.

\* \* \* \* \*